United States Patent
Arnold

(10) Patent No.: US 7,044,917 B2
(45) Date of Patent: *May 16, 2006

(54) METHOD AND APPARATUS FOR MEASURING PULSUS PARADOXUS

(75) Inventor: Donald Arnold, Nashville, TN (US)

(73) Assignee: Precision Pulsus, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,098

(22) Filed: Nov. 24, 2004

(65) Prior Publication Data

US 2005/0107712 A1    May 19, 2005

Related U.S. Application Data

(63) Continuation of application No. 10/228,641, filed on Aug. 27, 2002, now Pat. No. 6,869,402.

(51) Int. Cl.
*A61B 5/00* (2006.01)

(52) U.S. Cl. ................... 600/500; 600/485

(58) Field of Classification Search ......... 600/485–503
See application file for complete search history.

(56) References Cited

U.S. PATENT DOCUMENTS

| | | | |
|---|---|---|---|
| 5,297,548 A | 3/1994 | Pologe | |
| 5,849,706 A | 12/1998 | Molina Y Vedia et al. | |
| 5,873,359 A | 2/1999 | Zapol et al. | |
| 6,117,087 A | 9/2000 | Kamm et al. | |
| 6,129,675 A | 10/2000 | Jay | |
| 6,325,761 B1 | 12/2001 | Jay | |
| 6,334,065 B1 | 12/2001 | Al-Ali et al. | |
| 6,363,268 B1 | 3/2002 | Hanna et al. | |
| 6,385,471 B1 | 5/2002 | Mortz | |
| 6,869,402 B1 * | 3/2005 | Arnold | 600/500 |
| 2002/0013538 A1 | 1/2002 | Teller | |

OTHER PUBLICATIONS

M. Shamir, et al., *Pulse oximetry plethysmographic waveform during changes in blood volume*, British Journal of Anaesthesia, (1999) 82 (2): pp. 178-181.

J. Beatty and C. Figueroa, *Period analytic algorithms for the estimation of selected spectral properties of short segments of EEG data*, Behavior Research Methods & Instrument, 1974, vol. 6, No. 2, pp. 293-295.

(Continued)

*Primary Examiner*—Robert L. Nasser
(74) *Attorney, Agent, or Firm*—Knobbe, Martens, Olson & Bear, LLP

(57) ABSTRACT

A method and apparatus are disclosed of utilizing a source of arterial and/or arteriolar pulse waveform data from a patient for the purpose of measuring pulsus paradoxus. The arterial pulse waveform data source described is a pulse oximeter plethysmograph but can be any similar waveform data source, including intra-arterial transducer, blood pressure transducer, or plethysmograph. Through incorporation of the measurements of values, such as the area under the pulse waveform curve, that are time-domain functions of a change in height of the pulse waveform over at least a partial duration of the waveform, embodiments of the present invention represent a significant improvement upon previously described methods of measuring pulsus paradoxus and, further, produce improved accuracy in measurement of the multiple contributing variables generating pulsus paradoxus, in particular the contribution of diastolic events, to the extent that the physical signs so measured can be regarded as "Revised Pulsus Paradoxus."

8 Claims, 4 Drawing Sheets

OTHER PUBLICATIONS

T. Hartern, M.D., et al., *Use of Pulsus Oximetry to Recognize Severity of Airflow Obstruction in Obstructive Airway Disease, Correlation With Pulsus Paradoxus, Clinical Investigations in Critical Care.* CHEST, vol. 115 (2), Feb. 1999, pp. 475-481.

A. Awad, M.D., et al., *Different Responses of Ear and Finger Pulse Oximeter Wave From to Cold Pressor Test, Technology Computing and Simulation,* Anesthesia Analg., 2001; vol. 92, pp. 1,482-1,486.

W. B. Murray & P.A. Foster, *The Peripheral Pulse Wave: Information Overlooked,* al of Clinical Monitoring, Sep. 1996, vol. 12, No. 5, pp. 365-377.

C. Anthony Ryan, *Detection of Pulsus Paradoxus by Pulse Oximetry, AJDC. The Pediatric Forum,* May 1998, Letter to Editor, vol. 142, p. 481-482.

V. Chadwick, et al., *Continuous non-invasive assessment of pulsus paradoxus,* The Lancet, Feb. 22, 1992, vol. 339, pp. 495-496.

K. C. Bilchick, et al., *Paradoxical physical findings described by Kussmaul: pulsus paradoxus and Kussmaul's sign,* The Lancet, Jun. 1, 2002, vol. 359 Issue 9321, pp. 1940-1942.

D.W. Steele, MD., et al., *Continuous Noninvasive Determination of Pulsus Paradoxus: A Pilot Study,* Academic Emergency Medicine, Oct. 1995, 2 (10): 894-900.

* cited by examiner

METHOD AND APPARATUS FOR MEASURING PULSUS PARADOXUS

CROSS-REFERENCE TO RELATED APPLICATION

This application is a continuation application of U.S. patent application Ser. No. 10/228,641, filed Aug. 27, 2002 now U.S. Pat. No. 6,869,402, and entitled "Method and Apparatus for Measuring Pulsus Paradoxus," the entirety of which is hereby incorporated by reference.

FIELD OF THE INVENTION

Embodiments of the invention arise in the field of medical diagnosis, prognosis, and monitoring of patients afflicted with a variety of diseases and clinical syndromes such as asthma, croup, tension pneumothorax, pericardial tamponade, pulmonary embolus, hypovolemic shock, and sleep apnea. In particular, the invention relates to an improved non-invasive system and method for monitoring the presence and degree of pulsus paradoxus within a patient. The invention is particularly useful for rapidly assessing the status of a patient in acute respiratory distress in order to more accurately and objectively determine the severity of the patient's condition.

BACKGROUND OF THE INVENTION

Pulsus paradoxus is a medical term referring to a quantifiable, exaggerated decrease in arterial blood pressure during inspiration. In normal patients, this decrease is in the range of about 2–5 mm Hg; whereas, in a patient suffering from certain medical conditions, pulsus paradoxus can reach 10 mm Hg or higher. Pulsus paradoxus has been noted in a variety of medical conditions including, but not limited to, upper airway obstruction, bronchial asthma, tricuspid atresia, mitral stenosis, conditions of decreased left ventricular compliance, croup, tension pneumothorax, pericardial tamponade, pulmonary embolism, hypovolemic shock, and sleep apnea.

Asthma and Related Diseases

Asthma accounts for almost two million Emergency Department admissions annually in the U.S., and it is estimated that 29 million people will be diagnosed with asthma in the next two decades. Hospitalizations for childhood asthma have increased 3% to 5% annually, and mortality from asthma has increased 10% annually since 1977. Other forms of lung disease, including but not limited to chronic obstructive pulmonary disease ("COPD") and emphysema, place a heavy burden on patients and on the system of medical care. Early recognition and accurate assessment of the severity of airway obstruction and of the response to therapy are fundamental to the improvement of health for persons with these disorders.

Common measures used currently to assess the severity of asthma are clinical assessment, arterial blood gas analysis, spirometry, and pulse oximetry; however, all are subject to certain shortcomings. Clinical assessment scores, for example, exhibit marked interobserver variability and have been incompletely validated. Arterial blood gas analysis is an invasive and painful technique and is often complicated by therapeutic administration of O2 and β-adrenergic drugs and is therefore unreliable as an indicator of asthma severity. Tests of forced expiratory flow, as in spirometry, are effort dependent, typically cannot be used with children, and can actually exacerbate the underlying disease process. In part because physicians' ability to accurately assess pulmonary signs can be unreliable, numerous clinical scoring systems and management guidelines have been established for diseases such as asthma.

Despite the publication of the National Heart Lung and Blood Institute ("NHLBI") Guidelines for Emergency Department Asthma Management in 1991, the asthma mortality rate in children ages 5–17 nearly tripled between 1980 and 1996. Many experts are at a loss to explain the rising mortality of asthmatic patients in view of the improving quality of acute pharmacological management of asthma and the enhanced sophistication of emergency physicians and pre-hospital care systems. One explanation lies in the observation that there has been little change in how the acute asthmatic patient is evaluated. A recent development in assessing acute asthma has been the use of pulse oximetry (SPO2) which measures the degree of oxygen saturation of hemoglobin non-invasively and empirically. Despite the ubiquitous availability of pulse oximetry, (-adrenergic drugs, used widely, can result in ventilation-perfusion mismatch, leading to a fall in SPO2 even though the patient is improving. Finally, changes in SPO2 reflect atelectasis and intrapulmonary shunting and do not directly provide information regarding airflow obstruction and ventilation. An easily recognized, sensitive and objective parameter, by which practitioners of all levels of expertise could quickly recognize an asthma exacerbation, would help in more accurate diagnoses.

Easily measured, objective and accurate indices of severity for acute exacerbation of bronchiolitis, croup, emphysema and COPD are also not available. Additionally, medical emergencies such as cardiac tamponade, hypovolemia, and pulmonary embolism are difficult to diagnose and/or to quantify in severity. Finally, the response of these disorders to treatment is likewise difficult to objectively measure.

Traditional Methods of Pulsus Paradoxus Measurement

Although measurement of pulsus paradoxus is recommended by numerous authoritative medical practice guidelines (for example, the previously cited NHLBI Guidelines for Emergency Department Asthma Management), pulsus paradoxus is rarely recorded in clinical practice. Resistance by physicians to the application of pulsus paradoxus for the objective assessment of disease severity, and asthma in particular, is largely due to the difficulty in measuring pulsus paradoxus in a rapidly breathing patient by currently employed methods.

One conventional method of measuring pulsus paradoxus is through the use of intra-arterial catheters. Although intra-arterial catheters can often give reliable measurements of pulsus paradoxus, placement of these catheters is painful and associated with significant risk. Furthermore, placement of intra-arterial catheters should only be done by highly trained medical personnel using sophisticated monitoring equipment, preferably in a hospital setting. Consequently, this method is not favored for general use.

Another method for measuring pulsus paradoxus is with the use of a sphygmomanometer, commonly referred to as a blood pressure cuff. This technique involves inflating the sphygmomanometer to above systolic pressure and slowly deflating it. As the elevated systolic pressure occurring during expiration is approached, heart sounds will be heard intermittently (during expiration only), and as the lower systolic pressure occurring during inspiration is approached, heart sounds will be heard continuously. The difference between these points at which heart sounds are heard, first intermittently and then continuously, is a patient's pulsus paradoxus. However, this traditional method of measurement is difficult in the clinical setting in which noise, rapid respiratory rates and patient movement are the norm, and provides measurement of pulsus paradoxus at only a single point in time. Moreover, this process is ergonomically very difficult to perform and multiple operator efforts are typically required. As a result, the method is often inaccurate and unreliable. Manually derived pulsus paradoxus also correlates poorly with pulsus paradoxus calculated from intra-arterial pressure and, despite the NHLBI's recommendations, actual measurement of pulsus paradoxus is rare.

A third method of measuring pulsus paradoxus has been developed through photoplethysmographic techniques. In the field of photoplethysmography, pulses of light having different wavelengths are transmitted through or reflected by a patient's tissue to non-invasively determine various blood analyte values. More particularly, a photoplethysmographic device known as a pulse oximeter is employed to determine pulse rates and blood oxygen levels. Pulse oximeters typically include a probe that is attached to a patient's appendage (e.g., finger, ear lobe or nasal septum). The probe directs light signal pulses generated by a plurality of emitters through the appendage, wherein portions of the light signals are absorbed by the tissue. The intensity of light transmitted by the tissue is monitored by one or more detectors which output signals indicative of the light absorbency characteristics of the tissue. Because the blood analytes of interest each differentially absorb more light at one wavelength than at other wavelengths, the ratio of detector output signals can be used to compute the blood analyte concentrations.

By way of primary example, it is known that oxyhemoglobin (O2Hb) absorbs light more readily in the infrared region than in the red region, whereas reduced hemoglobin (RHb), or deoxyhemoglobin, more readily absorbs light in the red region than in the infrared region. As such, oxygenated blood with a high concentration of oxyhemoglobin and a low concentration of reduced hemoglobin will tend to have a high ratio of optical transmissivity in the red region to optical transmissivity in the infrared region. The relative transmissivity of blood at red and infrared center wavelengths can be employed as a measure of blood oxygen saturation (SpO2).

It is also recognized that concentrations of other related blood constituents (e.g., carboxyhemoglobin (COHb) and methemoglobin (MetHb)) can be measured with a similar approach since such analytes also have unique light absorbency characteristics at different corresponding wavelengths. The determination of such additional constituents can serve to enhance the measurement of blood oxygen saturation.

As will be appreciated by one skilled in the art, the detector output signal in pulse oximeters contains non-pulsatile and pulsatile components. The non-pulsatile component is influenced by the absorbency of tissue, venous blood, capillary blood, non-pulsatile arterial blood, the intensity of the light signals, ambient environmental light, and the sensitivity of the detector. The pulsatile component reflects the expansion of the arteriolar bed with arterial blood, and the varying amplitude of this pulsatile component depends upon the blood volume change per pulse as a result of arteriolar inflow. As such, the pulsatile component isolates the optical absorption attributable to the arterial blood component of the vascular bed and provides a basis for monitoring changes in the concentration of the noted blood analytes, oxyhemoglobin and deoxyhemoglobin. This feature of all plethysmographic oximeters, isolation of the pulsatile component of the arteriolar vascular bed and the waveform signal so generated, can be used to determine pulsus paradoxus for a particular patient.

Despite the problems inherent in these methods of detecting pulsus paradoxus, the advantages of measuring and monitoring pulsus paradoxus are significant. These measurements provide valuable insight into how troubled the act of breathing is for a given patient, and can help physicians detect, assess and treat numerous respiratory ailments. The NHLBI has recognized the advantages of measuring pulsus paradoxus and has recommended that pulsus paradoxus be measured on all asthmatic patients, despite inherent inaccuracies of the sphygmomanometric technique. Moreover, the NHLBI has advised that any patient with a pulsus paradoxus of 12 mm Hg or greater be hospitalized.

SUMMARY OF THE INVENTION

What is needed are new methods and systems for reliably measuring pulsus paradoxus and aiding in the examination, diagnosis and treatment of patients suffering from pulsus paradoxus-associated diseases. In particular, there is a need for an accurate, non-effort dependent, real-time, non-invasive apparatus and method for accurately measuring pulsus paradoxus. Embodiments of the present invention comprise a system and method to provide a sensitive, objective, accurate, real-time, painless and non-invasive parameter by which to assess these disorders.

In accordance with one aspect of the present invention, a method for measuring pulsus paradoxus in a mammal is provided. The method comprises obtaining data indicative of pulsatile cardiovascular behavior from the mammal, determining area under a curve for each of two or more measured pulse waveforms, and comparing the calculated areas to determine the presence or absence and magnitude of pulsus paradoxus.

In accordance with another aspect of the present invention, a system for measuring pulsus paradoxus in a mammal is provided. The system provided comprises a means for obtaining pulse waveform data indicative of pulsatile cardiovascular behavior from the mammal, a means for determining area under a curve from at least two pulse waveforms, and a means for comparing the calculated areas to determine the presence or absence and magnitude of pulsus paradoxus.

In accordance with another aspect of the invention, a system for measuring pulsus paradoxus in a mammal is provided. This system comprises a pulse oximeter that can obtain pulse waveform data indicative of pulsatile cardiovascular behavior from the mammal, a measurer that determines area under the curve from at least two pulse waveforms, and an analyzer that compares the calculated areas to determine the presence, absence and magnitude of pulsus paradoxus.

In accordance with another aspect of the invention, a method for measuring and/or detecting pulsus paradoxus in a mammal is provided. The method comprises obtaining data indicative of pulsatile cardiovascular behavior from the mammal, the data comprising at least a first and a second pulse waveform; determining a first value that is a time-domain function of a change in height of the first pulse waveform over at least a partial duration of the first pulse waveform; determining a second value that is a time-domain function of a change in height of the second pulse waveform over at least a partial duration of the second pulse waveform; comparing the first value and the second value to measure pulsus paradoxus.

Time-domain functions of a change in height of a pulse waveform over at least a partial duration of the pulse waveform include area under the curve (AUC), slope, average slope, maximal slope, and other functions. In some embodiments, there is generally no need to obtain frequency-domain information, such as that provided by Fourier transform or power spectral analysis, in order to make a determination of the presence and/or magnitude of pulsus paradoxus.

In accordance with other aspects of the invention, the method comprises obtaining data indicative of pulsatile cardiovascular behavior from a mammal, the data comprising a first plethysmographic or pressure amplitude obtained at a first time interval after an onset of a first pulse, and a second plethysmographic or pressure amplitude obtained at a second time interval after the onset of first pulse; determining a first value that is a time-domain function of a difference between the first and second plethysmographic or pressure amplitudes; obtaining a third plethysmographic or pressure amplitude obtained at the first time interval after an onset of a second pulse, and a fourth plethysmographic or pressure amplitude obtained at the second time interval after the onset of the second pulse; determining a second value that is a time-domain function of a difference between the third and fourth plethysmographic or pressure amplitudes; and comparing the first value and the second value to measure pulsus paradoxus.

As is well known in the field of plethysmography, a "plethysmographic amplitude" represents the magnitude of some measure of plethysmography, such as light transmission or absorption, and can reflect a magnitude of pressure in or volume of one or more vessels or chambers. Other factors, such as oxyhemoglobin (O2Hb), reduced hemoglobin (RHb), or deoxyhemoglobin, may also influence plethysmographic amplitude, as discussed previously. As used herein, "pressure amplitude" means blood pressure or a magnitude of absolute or relative blood pressure based on a system that uses a proxy for blood pressure, such as plethysmography.

Note that in obtaining a plethysmographic or pressure amplitude (or magnitude) at a time interval after an onset of a first pulse, this time interval may be of a fixed or predetermined duration, such as 0.2 sec or 0.3 msec, or it may be a relative time interval, such as the first half of systole or the 25–75% interval of the cardiac cycle or pulse duration. Also, this time interval can be set to zero (0), such that the plethysmographic or pressure amplitude at a time interval of zero after an onset of a pulse may itself equal zero, or any other baseline value of plethysmographic or baseline pressure amplitude that exists at the onset of the pulse.

BRIEF DESCRIPTION OF THE DRAWINGS

These and other aspects of this invention will be readily apparent from the detailed description below and the appended drawings, which are meant to illustrate and not to limit the invention, and in which.

DETAILED DESCRIPTION OF THE PREFERRED EMBODIMENT

Figure 1:
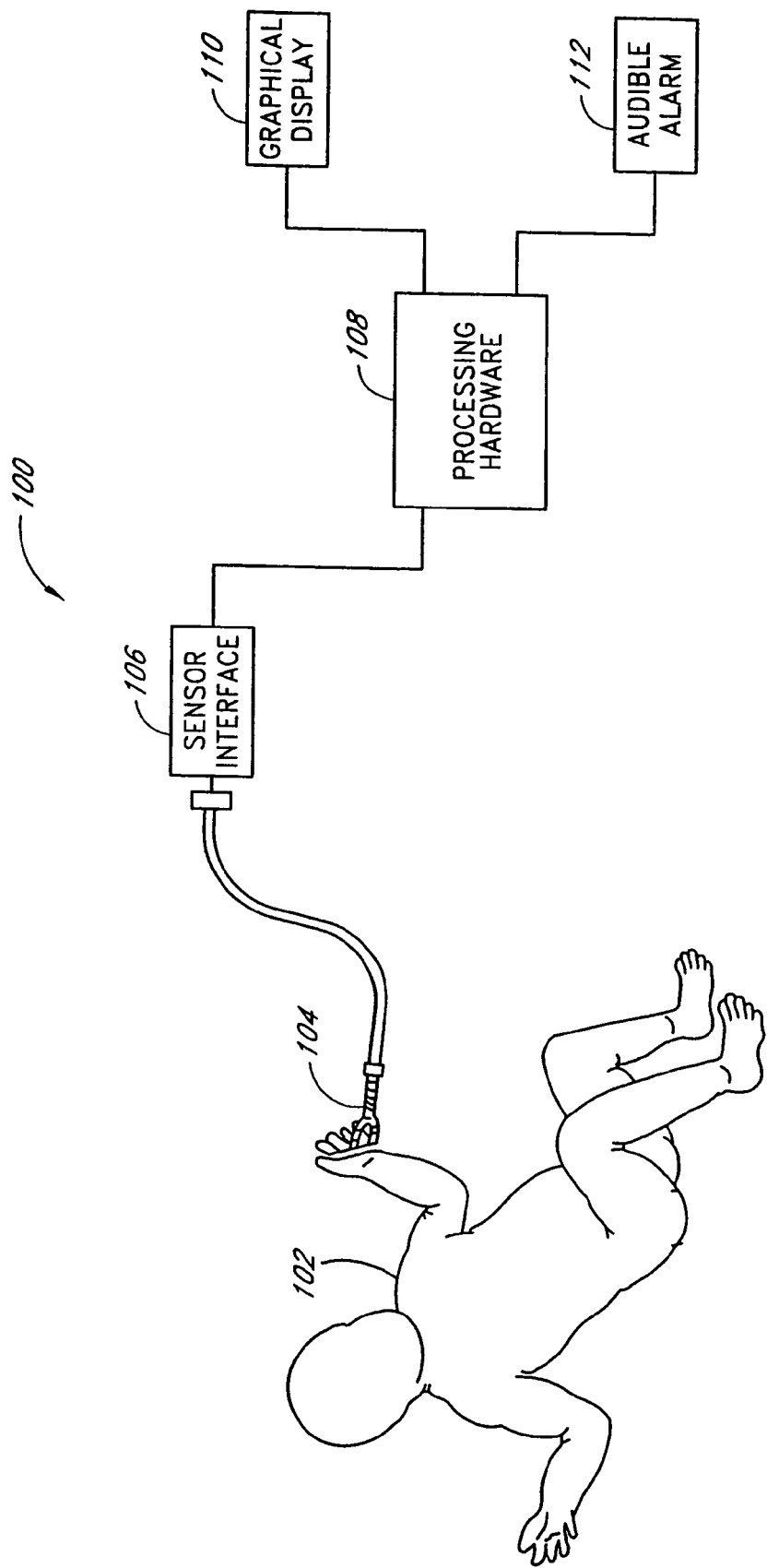
FIG. 1 depicts a pulse oximeter system connected to a mammalian patient.

Embodiments of the present invention will be more completely understood through the following detailed description, which should be read in conjunction with the attached drawings. In this description, like numbers refer to similar elements within various embodiments of the present invention.

Pulsus paradoxus represents a quantifiable, exaggerated decrease in arterial blood pressure during inspiration. Although frequently described in the medical literature as merely a decrease in systolic blood pressure, this physiologic phenomenon actually represents a decrease in left ventricular stroke volume ("LVSV") during the inspiratory phase of the respiratory cycle and/or an augmentation of LVSV during the expiratory phase of the respiratory cycle. This subtle distinction is important in development of the most accurate means by which to measure pulsus paradoxus.

The mechanisms of pulsus paradoxus are incompletely understood and can differ among various diseases. In severe acute asthma, for example, airway obstruction results from bronchospasm, mucous membrane edema and mucus plugging. Overcoming this obstruction to maintain airflow and ventilation necessitates the generation of increased negative intrapleural pressure on inspiration and increased positive intrapleural pressure on expiration. These exaggerated swings of intrapleural pressure result in increased left ventricular afterload during inspiration and decreased left ventricular afterload during expiration and concomitant decreased LVSV and increased LVSV during inspiration and expiration, respectively. Air-trapping and hyperinflation result in alveolar distension, pulmonary arteriolar vasoconstriction, and increased impedance to right ventricular ejection during inspiration. This results in decreased left ventricular filling and further impaired left ventricular stroke output. Diminished left ventricular filling also results from shift of the interventricular septum leftward as a result of augmented filling of the right ventricle. Conversely, these events are influenced inversely during expiration and result in increased LVSV during expiration. Each of these alterations contribute to paradoxical pulse in asthma and other respiratory and cardiovascular disease states.

More generally, pulsus paradoxus is caused by variably altering intrapleural pressure, left ventricular compliance, pulmonary hyperinflation, or systemic or pulmonary venous return. Any of these events, individually or collectively, lead to an accentuation of the decrease in LVSV during the inspiratory phase respiratory cycle and/or an augmentation of LVSV during the expiratory phase of the respiratory cycle, and thus the phenomenon of pulsus paradoxus. These changes in LVSV and resulting pulsus paradoxus have been demonstrated to result from the following physiologic events:

1. Increasingly negative intrapleural pressure during inspiration resulting in increased transmural (absolute intracardiac minus intrapleural) pressure.
2. Impairment to left ventricular ejection during inspiration resulting from increased afterload (as the left ventricular must create greater contractile force to overcome the increasingly negative intrapleural pressure).
3. Mechanical impairment to left ventricular filling (decreased compliance) due to shift of the interventricular septum leftward (resulting from increased venous return to the right heart as a result of increased negative intrapleural pressure during inspiration), resulting in decreased left ventricular stroke volume during inspiration.

4. Increased impedance to right ventricular ejection during inspiration due to increased alveolar volume and increased resistance to flow through alveolar capillaries, resulting in decreased pulmonary venous return to the left atrium and ventricle and decreased LVSV.

Typical methods of detecting pulsus paradoxus have numerous, significant disadvantages. For example, using intra-arterial catheters to detect pulsus paradoxus is painful, associated with significant risk and should only be done by highly trained medical personnel using sophisticated monitoring equipment, preferably in a hospital setting. Determining pulsus paradoxus through the use of a sphygmomanometer is often difficult and frequently results in unreliable readings. Through photoplethysmography, pulsus paradoxus can be determined in non-invasive fashion, but results can not be reliable and provide limited information to a physician or caregiver.

Previous attempts to quantify pulsus paradoxus from oximeter plethysmographic and other waveforms representing pulsatile arterial flow have done so by measuring changes in waveform height, a one-dimensional parameter, similar to the traditional methods described above, or by measuring variation of the plethysmograph baseline. Because pulsus paradoxus represents changes in LVSV and flow, these methods lack the sensitivity and accuracy of a method based upon two or three-dimensional parameters. Moreover, the existing techniques only measure changes in the height of the systolic waveform and do not adequately measure diastolic changes occurring during the cardiac cycle that contribute to pulsus paradoxus. The multiple physiologic events contributing to pulsus paradoxus and the corollary, that the diastolic and systolic contributions to pulsus paradoxus vary depending on the disease process involved, make evident the need to consider these diastolic contributions when measuring pulsus paradoxus. In the preferred embodiment, a method and system are provided which utilizes changes in area under a measured waveform curve ("AUC"), a two-dimensional parameter, to determine pulsus paradoxus. Preferably, the provided method and system also accurately incorporate diastolic changes in order to make a more sensitive and accurate assessment of the physiologic changes contributing to pulsus paradoxus.

FIG. 1 depicts a pulse oximeter system, generally designated as 100, connected to a mammalian patient 102. Preferably, pulse oximeter system 100 includes an optical transducer or probe 104, a sensor interface 106, processing hardware 108, a graphical display 110 and an audible alarm 112. In the preferred embodiment, the probe 104 is attached to the patient 102 on a digit, earlobe or other site overlying an arteriolar vascular bed. As illustrated in FIG. 1, the probe 104 can be attached to the fingers of the patient 102, but other locations are also possible. The probe 104 typically comprises an exterior housing that applies active elements of the probe 104 to tissue of the patient 102 containing an arterial or arteriolar vascular bed that is to be monitored. In the preferred embodiment, the probe 104 also contains one or more light-emitting diodes ("LEDs") and one or more light detectors to monitor the level of light transmitted through or reflected from the patient's 102 vascular tissue. The light detectors typically measure the changing optical absorption of light transmitted from LEDs at approximately 660 nm and 940 nm which results from volume expansion of the arteriolar and capillary beds during pulsatile cardiac blood flow. The probe transmits signals describing the detected light to at least one sensor interface 106. In addition, although a single probe 104 and a single sensor interface 106 are illustrated, one skilled in the art will recognize that alternative embodiments employing multiple probes 104 and/or multiple sensor interfaces 106 are also possible. One exemplary design of a typical pulse oximeter system is disclosed in U.S. Pat. No. 6,385,471 by Mortz, the entire disclosure of which is hereby incorporated by reference.

The signal received by the sensor interface 106 from the probe 104 is traditionally an analog signal and is preferably processed by additional analog circuitry and converted by an analog-to-digital converter circuit into a set of digital measurements before being transmitted to the processing hardware 108.

The processing hardware 108 can comprise a specific device, such as a digital signal processor specifically programmed or hardwired to implement the features of embodiments of the present invention. The processing hardware 108 can also comprise a general purpose computer, incorporating elements such as an Intel Pentium™ processor, physical memory, input and output devices, etc., programmed with software implementing features embodied by the present invention. The primary function of the processing hardware 108 is to measure the maximal change in area under a continuous optical plethysmographic waveform curve corresponding to arterial pulsation, to display data related to this measurement on the graphic display 110, and to trigger an audible alarm 112 to alert physicians or other caregivers to the presence and severity of pulsus paradoxus. The operation of the processing hardware 108 is described in additional detail below and, for the purpose of this disclosure, it is assumed that the other elements disclosed in FIG. 1 are the conventional components found in existing pulse oximeter systems.

Figure 2:
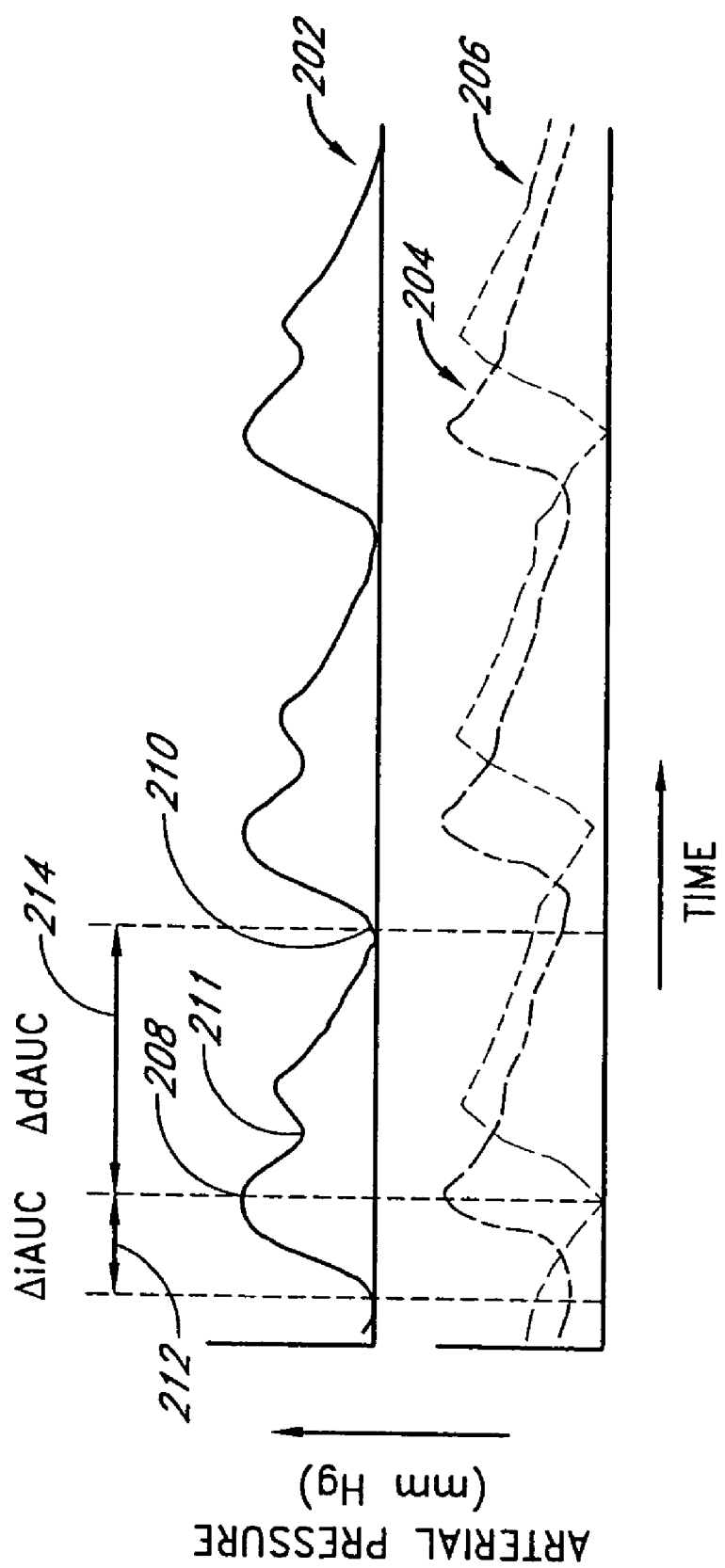
FIG. 2 depicts an arterial pressure waveform, in accordance with one aspect of the present invention.

FIG. 2 depicts an arterial pressure waveform 202, as detected by the pulse oximeter system 100. As is evident from the diagram, the waveform 202 represents the product of two distinct pressure waves flowing throughout the patient's 102 vascular system. Specifically, waveform 202 is comprised of an incident pressure wave component 204 and a reflected pressure wave component 206. The incident pressure wave component 204 represents the pressure wave created by the ventricular ejection of the heart of the patient 102, which travels through the circulatory system and causes blood vessels to expand. The reflected pressure wave component 206 represents the reflected wave traveling back through the blood vessels as they contract to their original size. Of note in the waveform 202 is its systole 208, its dicrotic notch 211 and its diastole 210. End systole 208 represents the highest point and end diastole represents the lowest point of arterial pressure. The dicrotic notch 211 represents closure of the aortic valve and the backsplash of blood against the closed valve.

Because the waveform 202 represents both systolic and diastolic pulsatile cardiac events, it is recognized to represent these individual events during different phases of the waveform 202. An ascending limb phase 212 (designated "iAUC") of the waveform 202, from the end (the lowest portion) of diastole 210 to the peak of systole 208 represents primarily LVSV. During the iAUC phase 212, the patient's 102 stroke volume expands the arterial tree and peripheral arteriolar and capillary tissue beds. The subsequent downstroke phase 214 (designated "dAUC") of the waveform 202 represents primarily outflow from the elastance vessels of the tissue bed, is influenced significantly by local vasomotor tone, and is much more variable than iAUC.

Figure 3:
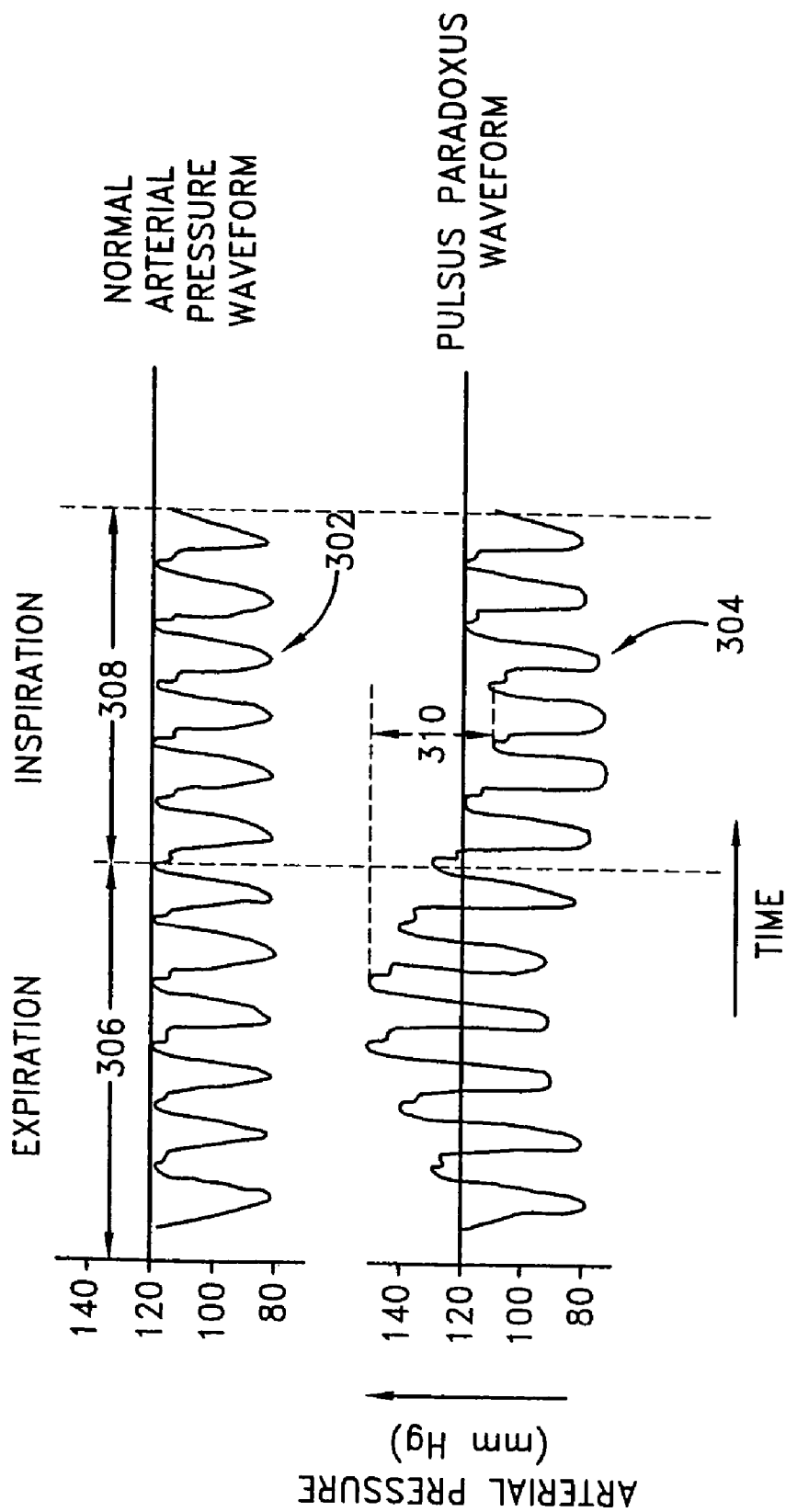
FIG. 3 depicts both a normal arterial pressure waveform and a pulsus paradoxus waveform, in accordance with another aspect of the present invention.

FIG. 3 depicts both a normal arterial pressure waveform 302 and a pulsus paradoxus waveform 304. As is evident from the diagram, in a healthy patient 102 (FIG. 1), arterial pressure is typically cyclic within a bounded range during both expiration 306 and inspiration 308. Here, the blood pressure illustrated in the normal waveform 302 is about 120 mm Hg/80 mm Hg. Systolic pressure varies little and, correspondingly, pulsus paradoxus is less than 5 mm Hg and is normal. However, in a patient with a condition generating pulsus paradoxus, peak arterial blood pressure can increase during expiration 306 and decrease during inspiration 308, as is evidenced by the pulsus paradoxus waveform 304. As indicated in FIG. 3, there is a change in peak height 310 of the waveform 304 between 110 mm Hg and 150 mm Hg and correspondingly, a pulsus paradoxus of 40 mm Hg.

Figure 4:
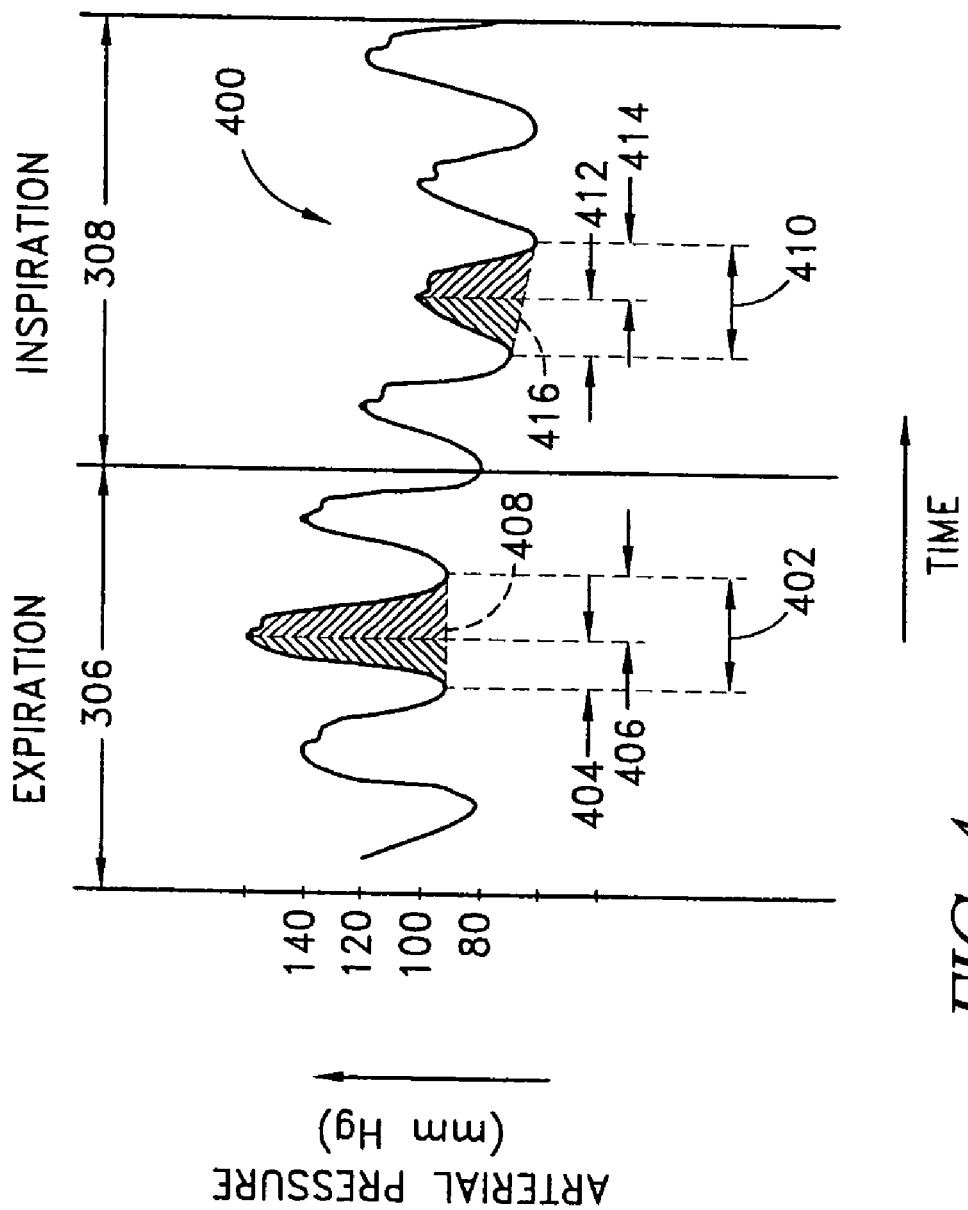
FIG. 4 illustrates measurements made upon a waveform through a preferred embodiment of the present invention.

FIG. 4 illustrates measurements made upon a waveform 400 through one embodiment of the present invention. This waveform 400 depicts arterial pressure in a typical patient 102, and it comprises a number of smaller periods, or components. In the preferred embodiment of the present invention, a first component 402 of the waveform 400 is selected by the processing hardware 108 (FIG. 1). As previously described, the first component 402 preferably includes an ascending limb phase 404 and a descending limb phase 406, which are bounded by the lowest portions of diastole and divided at the uppermost peak of systole. Preferably, a baseline 408 is then determined by the processing hardware 108, and the area under the curve component 402 and bounded by the baseline 408 is subsequently computed and stored. In alternate embodiments, the area under the curve component 402 during the ascending limb phase 404 and the descending limb phase 406 can also be computed. These computations will be readily apparent to one skilled in the art, and can be completed through integration, numerical approximation or summation, Fourier analysis, etc.

After calculating the area under the curve component 402, a second wave component 410 is selected. Preferably, the second component 410 also includes an ascending limb phase 412 and a descending limb phase 414, which are bounded by the lowest portions of diastole and divided at the uppermost peak of systole. Preferably, a baseline 416 is then determined by the processing hardware 108, and the area under the curve component 410 and bounded by the baseline 416 is subsequently computed and stored. In alternate embodiments, the area under the curve component 410 during the ascending limb phase 412 and the descending limb phase 414 can also be computed.

In the preferred embodiment, the AUC of components 402 and 410 are then compared to determine the presence and/or the magnitude of pulsus paradoxus. Preferably, the difference in the areas under the curve components 402, 410 ("$\Delta AUC$") is calculated as a percentage. As calculated by embodiments of the present invention, moderate airway obstruction and corresponding increases in pulsus paradoxus typically result in $\Delta AUC$ of greater than about 20–40%. Similarly, levels of $\Delta AUC$ greater than about 60% can result from and can be indicative of more severe airway obstruction and pulsus paradoxus. However, percent values of $\Delta AUC$ vary amongst individuals and may be valuable when determinations of $\Delta AUC$ are monitored in an individual longitudinally over time. In alternate embodiments, changes in iAUC and dAUC (designated "$\Delta iAUC$" and "$\Delta dAUC$", respectively) can also be measured and compared in a fashion similar to that provided herein for $\Delta AUC$, in order to provide additional information about the state of the patient 102.

While a single calculation of $\Delta AUC$ for two given curve components 402, 410, can often diagnose pulsus paradoxus and a variety of related ailments, the accuracy can be greatly improved by iteratively repeating the measurements and corresponding calculations, and analyzing the aggregate data from these measurements as it is collected. In this fashion, it is contemplated that a variety of alternate embodiments can be employed which make additional processing calculations, including: an average $\Delta AUC$ over a plurality of comparisons, a maximum and minimum $\Delta AUC$, a weighted or floating average for $\Delta AUC$, standard deviation and variance of AUC, artifact suppression, time interval measurement and adjustment, etc. In the preferred embodiment, weighted signal averaging would be employed to maximize the accuracy of the calculated pulsus paradoxus while maintaining minimal response times to changing pulsus paradoxus. Specifically, weighted signal averaging comprises calculating a rolling average of $\Delta AUC$ over a time interval. Advantageously, weighted signal averaging would assign a comparatively low weight to $\Delta AUC$ values obtained from individual intervals which fall significantly outside the current average $\Delta AUC$, thereby minimizing artifacts inherent in the pulsatile cardiovascular data. These, and other calculations will increase the efficacy of embodiments of the present invention by reducing the number of false positive reports (e.g., those due to arrhythmia) and increasing the system's overall accuracy.

Advantageously, embodiments of the system and methods provided herein reliably reflect corresponding increases or decreases in airway obstruction and pulsus paradoxus more accurately and less invasively than previous methods. Whether by pulse oximeter plethysmography, finger plethysmograph or other waveform, the preferred embodiment involves placing a non-invasive and painless transducer on a finger, ear lobe or other body area. The necessary calculations are conducted in real time, allowing for nearly instantaneous measurement of pulsus paradoxus, rapid notification for medical personnel, and quicker diagnosis and treatment. Furthermore, states of low perfusion, such as hypovolemia, will have little or no influence on the accuracy of pulsus paradoxus determined by embodiments of the present invention because the measurement of pulsus paradoxus is based upon relative changes $\Delta AUC$ during the respiratory cycle and not upon absolute values of AUC or other waveform indices.

In addition, the two dimensional parameters measured ($\Delta AUC$, $\Delta iAUC$ and $\Delta dAUC$) are far more accurate for determining the presence and/or magnitude of pulsus paradoxus than manual measurement or methods utilizing only change in waveform height. The decrease in LVSV that results in pulsus paradoxus is a change in volume, a three-dimensional entity. The two-dimensional mathematical waveform indices, including changes in area under the waveform curve which we utilize to measure pulsus paradoxus, accurately represent the true changes occurring in LVSV and, thus, pulsus paradoxus. Previous developers have not recognized the importance of utilizing this two-dimensional parameter, area under the curve, to measure pulsus paradoxus.

Furthermore, numerous advantages not realized under previous techniques are also achieved. For example:

1. The preferred embodiment does not require simultaneous determination of the phases of the respiratory cycle.
2. The preferred embodiment is based upon the percent change in AUC and, thus requires less intensive use of processing hardware and/or software, allowing less sophisticated and/or less expensive components to be used.

3. The preferred embodiment is not significantly influenced by changes in waveform baseline occurring as a result of movement of the patient 102.

4. Although the timing of events causing pulsus paradoxus during the respiratory cycle is altered during positive pressure ventilation, the preferred embodiment nonetheless provides accurate measurement of pulsus paradoxus during positive pressure ventilation.

In addition to the diagnosis of pulsus paradoxus, embodiments of the present invention allow for accurate and timely recognition of airway obstruction (e.g., from mucus plugs), mechanical failure (equipment failure), loss of the airway (tracheostomy tube displacement) or other conditions associated with pulsus paradoxus such as cardiac tamponade. Consequently, the methods and systems provided herein will aid in the rapid diagnosis and treatment of patients currently or potentially suffering from Sudden Infant Death Syndrome or obstructive sleep apnea. Technology dependent patients dependent on home assisted ventilation and artificial airways (tracheostomy) will also benefit from this monitoring.

Given the embodiments of the invention described herein, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalents thereof.

What is claimed is:

1. A method for measuring pulsus paradoxus in a mammal, the method comprising:

obtaining data indicative of pulsatile cardiovascular behavior from the mammal, the data comprising at least a first and a second pulse waveform;

Determining a first value that is a lime-domain function of a change in height of the first pulse waveform over at least a partial duration of the first pulse waveform;

Determining a second value that is a time-domain function of a change in height of the second pulse waveform over at least a partial duration of the second pulse waveform;

comparing the first value and the second value to measure pulses paradoxus.

2. The method of claim 1, further comprising determining the presence or absence of pulsus paradoxus.

3. The method of claim 1, further comprising correlating a magnitude of the difference between the first value and second value with a magnitude of pulsus paradoxus.

4. The method of claim 1, wherein the partial duration of the first pulse waveform is systole.

5. A method for measuring pulsus paradoxus in a mammal, the method comprising:

obtaining data indicative of pulsatile cardiovascular behavior from the mammal, the data comprising a first plethysniographic or pressure amplitude obtained at a first time interval after an onset of a first pulse, and a second plethysmographic or pressure amplitude obtained at a second time interval after the onset of the first pulse;

determining a first value that is a time-domain function of a difference between the first and second plethysmographic or pressure amplitudes;

obtaining a third plethysmographic or pressure amplitude obtained at the first time interval after an onset of a second pulse, and a fourth plethysmograph or pressure amplitude obtained at the second time interval after the onset of the second pulse;

determining a second value tat is a time-domain function of a difference between the third and fourth plethysmographic or pressure amplitudes; and comparing the first value and the second value to measure pulsus paradoxus.

6. The method of claim 5, further comprising determining the presence or absence of pulsus paradoxus.

7. The method of claim 5, further comprising correlating a magnitude of the difference between the first value and second value with a magnitude of pulsus paradoxus.

8. The method of claim 5, wherein the partial duration of the first pulse waveform is systole.

* * * * *

UNITED STATES PATENT AND TRADEMARK OFFICE
CERTIFICATE OF CORRECTION

| | | |
|---|---|---|
| PATENT NO. | : 7,044,917 B2 | Page 1 of 1 |
| APPLICATION NO. | : 10/997098 | |
| DATED | : May 16, 2006 | |
| INVENTOR(S) | : Donald Arnold | |

It is certified that error appears in the above-identified patent and that said Letters Patent is hereby corrected as shown below:

At column 11, Line 38, in Claim 1, please delete "lime-domain" and insert -- time-domain --, therefore.

At column 12, Line 2, in Claim 1, please delete "pulses" and insert -- pulsus --, therefore.

At column 12, Line 16, in Claim 5, please delete "plethysniographic" and insert -- plethysmographic --, At column 12, Line 27 (Approx.), in Claim 5, please delete "plethysmograph" and insert -- plethysmographic --, therefore.

At column 12, Line 30, in Claim 5, please delete "tat" and insert -- that --, therefor.

Signed and Sealed this

Twenty-eighth Day of November, 2006

JON W. DUDAS
*Director of the United States Patent and Trademark Office*